US00PP29665P3

(12) United States Plant Patent
Jachertz

(10) Patent No.: US PP29,665 P3
(45) Date of Patent: Sep. 11, 2018

(54) ***GASTERIA* PLANT NAMED 'D DUE'**

(50) Latin Name: ***Gasteria* hybrid**
Varietal Denomination: D Due

(71) Applicant: Christian Jachertz, Amposta (ES)

(72) Inventor: Christian Jachertz, Amposta (ES)

(73) Assignee: Deltacactus S.L., Amposta (ES)

( * ) Notice: Subject to any disclaimer, the term of this patent is extended or adjusted under 35 U.S.C. 154(b) by 51 days.

(21) Appl. No.: 15/530,429

(22) Filed: Jan. 12, 2017

(65) Prior Publication Data

US 2018/0199490 P1 Jul. 12, 2018

(51) Int. Cl.
*A01H 5/12* (2018.01)

(52) U.S. Cl.
USPC ..... Plt./373

CPC ..... *A01H 5/12* (2013.01)

(58) Field of Classification Search
USPC ..... Plt./373
See application file for complete search history.

(56) References Cited

PUBLICATIONS

UPOV-PLUTO: Plant Variety Database, Apr. 14, 2018, citation for 'D Due'. 1 page.*
Wander Tuinier BV Succulents: plants for professionals. Jul. 2016. https://issuu.com/dummenorange/docs/wander_tunier_brochurejuly2016. 4 pages.*

* cited by examiner

*Primary Examiner* — Susan McCormick Ewoldt
*Assistant Examiner* — Karen M Redden

(57) ABSTRACT

A new cultivar of *Gasteria* plant named 'D Due' that is characterized by a star-shaped rosette plant form and dark green glossy leaves with yellow-green dots.

1 Drawing Sheet

Botanical classification: *Gasteria* hybrid.
Variety denomination: 'D Due'.

BACKGROUND OF THE INVENTION

The present invention relates to a new and distinct cultivar of *Gasteria* plant botanically known as *Gasteria* hybrid and hereinafter referred to by the cultivar name 'D Due'.

The new *Gasteria* plant is a naturally occurring whole plant mutation of *Gasteria* 'WT10' (U.S. Plant Pat. No. 23,622). The new *Gasteria* plant was discovered and selected by the Inventor as a single plant within a population of plants of 'WT10' in a controlled environment in a cultivated area of Amposta, Tarragona, Spain in 2013.

Asexual reproduction of the new cultivar 'D Due' first occurred by leaf cuttings in 2014 in Amposta, Tarragona, Spain. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Gasteria* cultivar 'D Due'. These traits in combination distinguish 'D Due' as a new and distinct cultivar apart from other existing varieties of *Gasteria* known by the inventor.

1. *Gasteria* 'D Due' exhibits dark green glossy leaves with yellow-green dots.
2. *Gasteria* 'D Due' exhibits a star-shaped rosette plant form.

The closest comparison cultivars are *Gasteria* 'Green Star' (U.S. Plant Pat. No. 24,763) and *Gasteria* 'Royal Wolfgang' (U.S. Plant Pat. No. 25,667). 'D Due' is distinguishable from 'Green Star' by the following characteristics:

1. *Gasteria* 'D Due' exhibits a darker green leaf color than the leaf color of 'Green Star'.
2. *Gasteria* 'D Due' exhibits leaves with a glossy luster. In comparison, the leaves of 'Green Star' are duller in luster.
3. *Gasteria* 'D Due' exhibits leaves that are thicker than the leaves of 'Green Star'.

'D Due' is distinguishable from 'Royal Wolfgang' by the following characteristics:

1. *Gasteria* 'D Due' exhibits leaves with random yellow-green dots. In comparison, the leaves of 'Royal Wolfgang' have white dots that form a striped pattern.
2. *Gasteria* 'D Due' exhibits leaves with an entire leaf margin. In comparison, the leaves of 'Royal Wolfgang' have denticulate leaf margins with white teeth.
3. *Gasteria* 'D Due' exhibits leaves with a glossy luster. In comparison, the leaves of 'Royal Wolfgang' are duller in luster.
4. *Gasteria* 'D Due' exhibits leaves that are smaller in length and width than the leaves of 'Royal Wolfgang'.
5. *Gasteria* 'D Due' exhibits a more compact habit than the habit of 'Royal Wolfgang'.

'D Due' is distinguishable from the parent plant 'WT10' by the following characteristics:

1. *Gasteria* 'D Due' exhibits leaves that are darker green in color than the leaves of 'WT10'.
2. *Gasteria* 'D Due' exhibits leaves that are thicker than the leaves of 'WT10'.

BRIEF DESCRIPTION OF THE DRAWING

The accompanying photograph illustrates the distinguishing traits of *Gasteria* 'D Due'. The photograph shows an overall view of a 20 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Gasteria* cultivar named 'D Due'. Data was collected in Amposta, Tarragona, Spain from 20 week old plants grown in a glass greenhouse in 8.5 cm. diameter containers. The time of year was Spring and the temperature range was 20-25 degrees Centigrade during the day and 12-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'D Due' has not been tested under all possible conditions and phenotypic differences may be observed with variations in environmental, climatic, and cultural conditions, however, without any variance in genotype.

Botanical classification: *Gasteria* hybrid 'D Due'.

*Annual or perennial.*—Perennial.

*Parentage.*—'D Due' is a naturally occurring whole plant mutation of *Gasteria* 'WT10'.

*Growth habit.*—Basal rosette.

*Plant shape.*—Flattened globe shaped.

*Suitable container size.*—7.0 cm. pots or larger.

*Plant height.*—8.0 cm.

*Plant width.*—11.9 cm.

*Vigor.*—Low to moderate.

*Growth rate.*—Low to moderate.

*Low temperature tolerance.*—10° Centigrade.

*High temperature tolerance.*—35° Centigrade.

*Propagation.*—Leaf cuttings.

*Time to initiate roots* (*summer*).—14 days at 20° C.

*Time to initiate roots* (*winter*).—21 days at 20° C.

*Time to produce a rooted cutting* (*summer*).—28 days at 20° C.

*Time to produce a rooted cutting* (*winter*).—42 days at 20° C.

*Crop time.*—Approximately 35 weeks in Amposta, Tarragona, Spain.

*Root system.*—Thick and fibrous.

*Root color.*—N155A.

*Plant fragrance.*—None.

*Branching habit.*—Leaves arise in basal rosette, no branches.

Foliage:

*Leaf arrangement.*—Basal rosette.

*Compound or single.*—Single.

*Quantity of leaves per plant.*—Average 28.

*Leaf shape.*—Lanceolate, succulent.

*Leaf aspect.*—Flattened.

*Leaf apex.*—Long apiculate.

*Leaf base.*—Broad cuneate.

*Leaf dimensions.*—7.6 cm. in length, 2.1 cm. in width and 1.0 cm. in thickness.

*Leaf texture* (*upper surface*).—Pustulate orbicular dots, 1.0 mm. in diameter and 1.0 mm. in height.

*Leaf texture* (*lower surface*).—Pustulate orbicular dots, 1.0 mm. in diameter and 0.8 mm. in height.

*Leaf luster* (*upper surface*).—Glossy.

*Leaf luster* (*lower surface*).—Moderately glossy.

*Leaf rugose.*—Not rugose.

*Leaf lobed.*—Not lobed.

*Pubescence.*—Absent.

*Leaf margin.*—Entire with pustulate orbicular dots 1.0 mm. in diameter and 1.0 mm. in height.

*Venation pattern.*—None visible.

*Young leaf color* (*upper surface*).—139A, fading towards base 146D, pustulate orbicular dots 146C.

*Young leaf color* (*lower surface*).—Between NN137A and 139A, fading towards base 146D, postulate orbicular dots 146C.

*Mature leaf color* (*upper surface*).—Between 139A and 147A, fading towards base 147C to 147D, pustulate orbicular dots 146C.

*Mature leaf color* (*lower surface*).—Between 139A and 147A, fading towards base 147D, pustulate orbicular dots 146C.

Flower: 'D Due' has not produced flowers to date.

Fruit and seed: 'D Due' has not produced fruit or seed to date.

Disease and pest resistance: Disease and pest resistance has not been observed.

The invention claimed is:

1. A new and distinct variety of *Gasteria* plant named 'D Due' as described and illustrated.

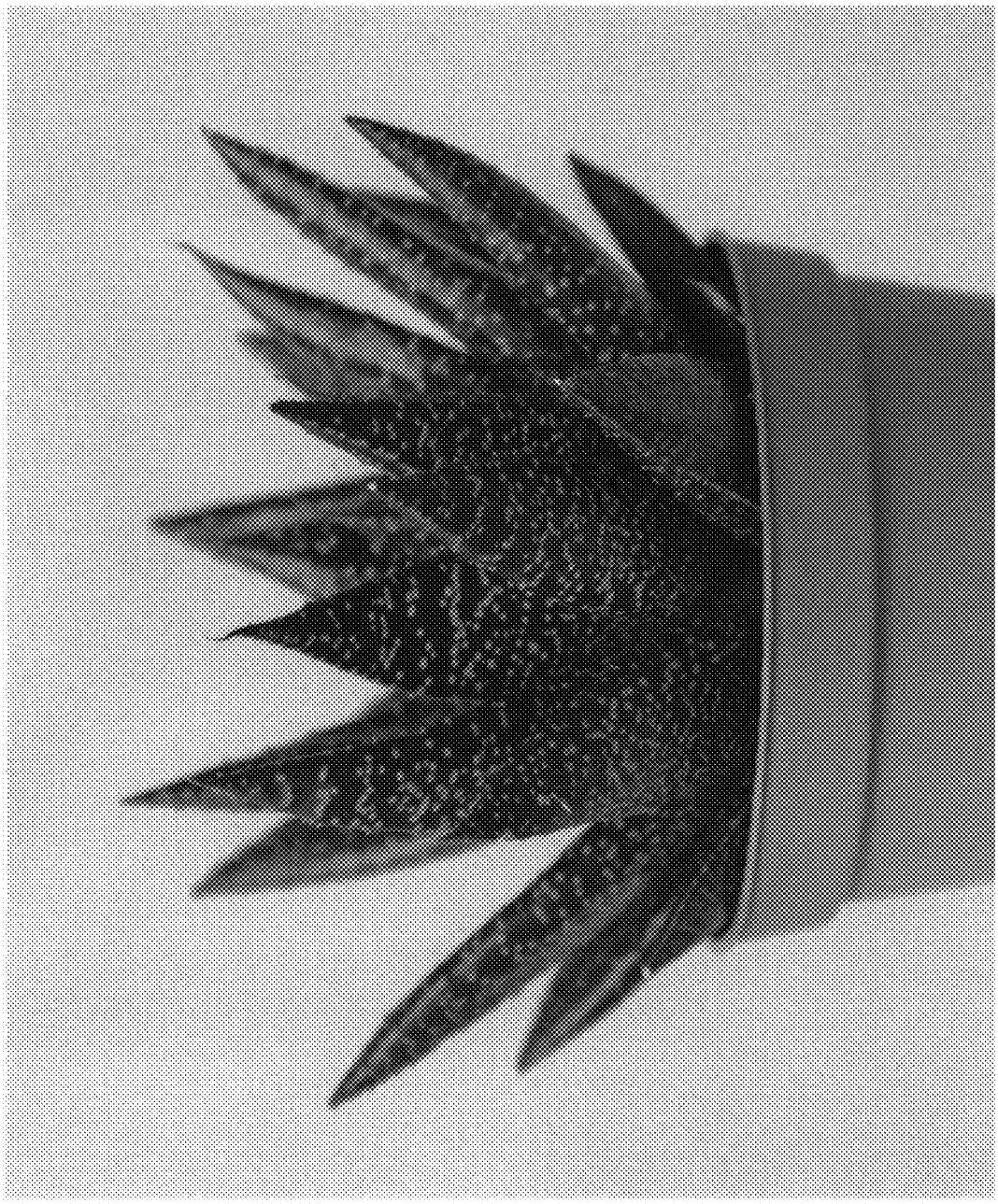

* * * * *